United States Patent [19]

Tao et al.

[11] 4,346,225

[45] Aug. 24, 1982

[54] HERBICIDAL 2-METHYLAMINO THIADIAZOLINES

[75] Inventors: Eddie V. P. Tao; Gilbert S. Staten, both of Indianapolis, Ind.

[73] Assignee: Eli Lilly and Company, Indianapolis, Ind.

[21] Appl. No.: 273,697

[22] Filed: Jun. 15, 1981

[51] Int. Cl.$^3$ ............................................. C07D 285/12
[52] U.S. Cl. ........................................ 548/138; 71/90
[58] Field of Search ......................................... 548/138

[56] References Cited

FOREIGN PATENT DOCUMENTS 1195672 6/1970 United Kingdom .
1266172 3/1972 United Kingdom .
1276925 6/1972 United Kingdom .
1297147 11/1972 United Kingdom .

OTHER PUBLICATIONS

Yandovskii et al.; Chem. Abs. 84:150572 (1976).
Yandovskii et al.; Chem. Abs. 85:21223 (1966).
Werber, Chem. Abs. 83:97116 (1975).
Werber; Chem. Abs. 84:74184 (1976).

Primary Examiner—Mary C. Lee
Attorney, Agent, or Firm—Joseph A. Jones; Arthur R. Whale

[57] ABSTRACT

4-Acyl-2-methylamino-4,5-dihydro-1,3,4-thiadiazoles are herbicides active against pigweed and foxtail.

10 Claims, No Drawings

HERBICIDAL 2-METHYLAMINO THIADIAZOLINES

BACKGROUND OF THE INVENTION

1. Field of the Invention

This invention belongs to the field of agricultural chemistry, and provides a series of new herbicides which are 2-methylamino-4-acyl-4,5-dihydro-1,3,4-thiadiazoles. The compounds are particularly useful for the preemergence control of pigweed (Amaranthas species) and foxtail (Setaria species).

2. State of the Art

The thiadiazol-2-ylureas have been studied as herbicides for some years, especially as herbicides for the total control of vegetation. Patent publications which are typical include South African Pat. No. 69/1559, of Cebalo, and British Pat. Nos. 1,297,147, of Metzger et al., 1,276,925, of Rucker et al., 1,195,672, of Mobil Oil Corp., and 1,266,172, of Air Products and Chemicals Company. Such compounds are fully unsaturated thiadiazoles, and have a urea group with various substitutions at the 2-position of the thiadiazole ring.

Other interesting publications include Yandovskii and Zamorina, *Zh. Org. Khim.* 12, 457–61 (1976), C.A. 85, 21223 (1976), showing 4-acetyl-5,5-dialkyl-2-(H or methyl)-4,5-dihydro-1,3,4-oxadiazoles, and Yandovskii et al., *Zh. Org. Khim.* 12, 435–39 (1976), showing related oxadiazolines; and Werber et al., *J. Het. Chem.* 12, 841–44 (1975), C.A. 84, 74184 (1976), and *J. Het. Chem.* 12, 581–83 (1975), C.A. 83, 97116 (1975), showing 2-acyl-4-alkyl-5-imino-4,5-dihydro-1,3,4-thiadiazoles.

SUMMARY OF THE INVENTION

This invention provides a series of compounds of the formula

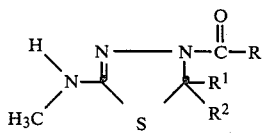

wherein R is phenyl, 3-trifluoromethylphenyl, 2-trifluoromethylphenyl, fluorophenyl, chlorophenyl, nitrophenyl, or $C_3$-$C_4$ alkyl; $R^1$ and $R^2$ are independently hydrogen, methyl or ethyl, provided that one of $R^1$ and $R^2$ is not methyl when the other is ethyl, and provided that no more than one of $R^1$ and $R^2$ is hydrogen.

DESCRIPTION OF THE PREFERRED EMBODIMENT

Throughout this document, temperatures are expressed in degrees Celsius. The term $C_3$-$C_4$ alkyl refers to the groups propyl, isopropyl, butyl, isobutyl, s-butyl and t-butyl.

It is believed that the compounds which are provided by this invention are entirely clear from the above formula. However, a few typical compounds will be mentioned for the convenience of the reader.

4-(2-chlorobenzoyl)-5,5-diethyl-2-methylamino-4,5-dihydro-1,3,4-thiadiazole 4-(4-chlorobenzoyl)-5,5-dimethyl-2-methylamino-4,5-dihydro-1,3,4-thiadiazole 4-butyryl-5-ethyl-2-methylamino-4,5-dihydro-1,3,4-thiadiazole 5-methyl-4-(2-methylpropionyl)-2-methylamino-4,5-dihydro-1,3,4-thiadiazole 5,5-dimethyl-2-methylamino-4-pivaloyl-4,5-dihydro-1,3,4-thiadiazole 2-methylamino-4-(2-methylbutyryl)-5,5-dimethyl-4,5-dihydro-1,3,4-thiadiazole 5-ethyl-2-methylamino-4-(3-methylpropionyl)-4,5-dihydro-1,3,4-thiadiazole 5-methyl-2-methylamino-4-valeryl-4,5-dihydro-1,3,4-thiadiazole The compounds of this invention are prepared by reacting 4-methylthiosemicarbazide with the appropriate ketone or aldehyde, having the $R^1$ and $R^2$ substituents, to prepare a starting compound of the formula

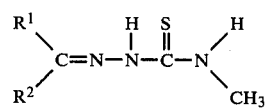

The above starting compound is reacted with the appropriate acyl chloride,

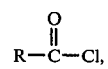

in the presence of pyridine, to cyclize the starting compound and prepare the thiadiazolin-2-ylamine. The process goes very readily at moderate temperatures, and in a single vessel. It has been found to be preferable first to dissolve the methylthiosemicarbazide in the ketone or aldehyde to bring about the first step of the reaction. Of course, it is quite possible to carry the reaction out in another solvent, in order to require less of the possibly expensive ketone or aldehyde. The usual types of inert organic solvents used for reactions may be used in this step, such as aromatics, including benzene, toluene, xylene and the like, ethers, such as diethyl ether, tetrahydrofuran, diisopropyl ether and the like, esters including ethyl acetate, ethyl propionate and the like, and halogenated alkanes.

When the reaction with the ketone or aldehyde has gone as far as is desired, the cyclization is brought about by simply adding pyridine and the acyl chloride to the mixture.

It is preferred to carry out both steps of the above process at about ambient temperature, but moderate reaction temperatures in the range of from about 0° to about 65° may be used as desired. The cyclization step, brought about by the addition of the acyl chloride, is exothermic, and it is advisable to cool the vessel while the acyl chloride is added slowly to the mixture with good stirring.

In general, all of the reaction steps described above need only the stoichiometric proportions of the various reactants. The possible exception is the reaction with the ketone or aldehyde, where it is convenient to use that reactant as the solvent as well. Although only the stoichiometric amounts of the reactants are necessary, it will be understood that it is often advantageous to use a moderate excess of a reactant, in order to assure that a more expensive or hard to obtain reactant is fully consumed. For this purpose, small excess amounts in the range of from about 1 or 2% to about 50% may be used as convenient; larger excess amounts do no harm.

The following examples further illustrate the synthesis of the compounds of this invention.

EXAMPLE 1

2-Methylamino-5,5-dimethyl-4-pivaloyl-4,5-dihydro-1,3,4-thiadiazole

A 52.5 g. portion of 4-methylthiosemicarbazide was suspended and partially dissolved in 250 ml. of acetone, and 39.5 g. of pyridine was added. The mixture was stirred for 15 minutes at ambient temperature, and then 60.5 g. of pivaloyl chloride was added slowly while the temperature of the reaction mixture was held at 20°–25°. The mixture was stirred at ambient temperature for 3 hours after the addition, and then 200 ml. of water was added. The reaction mixture was filtered, and the filter cake was washed with 100 ml. of nitromethane and vacuum dried at 50° to obtain 91.4 g. of the desired intermediate product, m.p. 162°–164°.

EXAMPLE 2

2-Methylamino-5-methyl-4-pivaloyl-4,5-dihydro-1,3,4-thiadiazole

A 10.5 g. portion of 4-methylthiosemicarbazide was combined with 4.4 g. of acetaldehyde, and 7.9 g. of pyridine and 200 ml. of toluene were added. The mixture was stirred for a short time, and 12.1 g. of pivaloyl chloride was added slowly with agitation while the temperature of the mixture was held at 20°–25°. The mixture was then stirred at ambient temperature for 3 hours, and 50 ml. of water was added. The layers were separated, and the toluene layer was washed with water and was then concentrated under vacuum to obtain 21 g. of oil. The oil was dissolved in 25 ml. of hot nitromethane, filtered and cooled gradually to obtain a solid, which was washed with cold nitromethane and vacuum dried at 50° to obtain 14.8 g. of impure product, which was purified by slurrying it twice with 25 ml. portions of cold nitromethane and vacuum drying to obtain 8.3 g. of product, m.p. 102°–103°.

EXAMPLE 3

5-Ethyl-2-methylamino-4-pivaloyl-4,5-dihydro-1,3,4-thiadiazole

A 10.5 g. portion of 4-methylthiosemicarbazide was reacted with 5.8 g. of propionaldehyde in the presence of 7.9 g. of pyridine and 200 ml. of toluene, and 12.1 g. of pivaloyl chloride was added to produce 13.8 g. of the desired product, m.p. 78.5°–80°.

EXAMPLE 4

4-(2-Fluorobenzoyl)-2-methylamino-5,5-dimethyl-4,5-dihydro-1,3,4-thiadiazole

A 42 g. portion of 4-methylthiosemicarbazide was reacted with 400 ml. of acetone, and then with 32 ml. of pyridine and 63.6 g. of 2-fluorobenzoyl chloride to prepare 66.5 g. of the desired product, m.p. 136°–140°.

EXAMPLE 5

2-Methylamino-5,5-dimethyl-4-(2-trifluoromethylbenzoyl)-4,5-dihydro-1,3,4-thiadiazole A 42 g. portion of 4-methylthiosemicarbazide was reacted with 200 ml. of acetone, and then with 31.6 g. of pyridine and 83.6 g. of 2-trifluoromethylbenzoyl chloride to obtain a recrystallized yield of 70.1 g. of the desired product, m.p. 164°–169°.

EXAMPLE 6

5,5-Dimethyl-2-methylamino-4-(3-nitrobenzoyl)-4,5-dihydro-1,3,4-thiadiazole

A 21 g. portion of 4-methylthiosemicarbazide was reacted with 200 ml. of acetone at ambient temperature for 16 hours, and then 16 ml. of pyridine and 37.1 g. of 3-nitrobenzoyl chloride were added and the mixture was stirred for 3 hours at ambient temperature. Two hundred ml. of water was added, the mixture was stirred for 1 hour, the layers were separated, and the organic layer was evaporated to an oil under vacuum. The oil solidified upon standing overnight, and was recrystallized from hot acetone to obtain 26.3 g. of crude product, which was recrystallized again from 15 ml. of hot nitromethane to obtain 21.4 g. of product, m.p. 130°–133°.

EXAMPLE 7

4-Benzoyl-5,5-dimethyl-2-methylamino-4,5-dihydro-1,3,4-thiadiazole

A 42 g. portion of 4-methylthiosemicarbazide was reacted with 23.2 g. of acetone in 500 ml. of toluene as described in Example 1, except that the mixture was heated briefly to reflux, and then cooled to 70°, before 32 ml. of pyridine was added. Then the mixture was cooled to 20°, and 56.3 g. of benzoyl chloride was added. The reaction mixture was worked-up substantially as described in Example 1 to obtain 31.8 g. of the desired product, m.p. 130°–136°.

EXAMPLE 8

4-(4-Fluorobenzoyl)-5,5-dimethyl-2-methylamino-4,5-dihydro-1,3,4-thiadiazole

A 42 g. portion of 4-methylthiosemicarbazide was reacted with 400 ml. of acetone, and then with 32 ml. of pyridine and 63.6 g. of 4-fluorobenzoyl chloride, and the mixture was worked-up as described in Example 1. The product was recrystallized from 80 ml. of nitromethane to obtain 43 g. of the desired product, 138°–144°.

EXAMPLE 9

5,5-Dimethyl-2-methylamino-4-(3-trifluoromethylbenzoyl)-4,5-dihydro-1,3,4-thiadiazole A 42 g. portion of 4-methylthiosemicarbazide was reacted with 200 ml. of acetone, and then with 32 g. of pyridine and 83.6 g. of 3-trifluoromethylbenzoyl chloride. The mixture was worked-up as described in Example 1 to obtain 77.5 g. of the desired product, m.p. 111°–115°, after recrystallization from nitromethane.

The compounds of this invention have been tested to determine the range of their herbicidal efficacy. Representative tests are reported below. The results of the tests are reported on a 1–5 scale, on which 1 indicates normal plants and 5 indicates no emergence of seeds or dead plants.

Seeds of the species to be tested were planted in flat metal trays, in a sandy sterilized soil, and each flat was individually fertilized.

The compound to be tested was formulated in 1:1 acetone:ethanol at the rate of 6 g. per 100 ml., together with 2 g. per 100 ml. of an anionic-nonionic surfactant blend, and 1 part of the organic solution was diluted with 12 parts of water for application.

Application of the compounds at 9 kg./ha. was made postemergence in some cases and preemergence in others. Postemergence applications were sprayed over the emerged plants about 12 days after the seeds were planted, and preemergence applications were sprayed on the soil the day after the seeds were planted. After the compounds were applied, the trays were moved to the greenhouse, watered as necessary, and observed and rated about 10-13 days after application of the compounds. Untreated control plants were used as standards in every test.

The table below reports results of testing typical compounds of the invention, which are identified by their example numbers above.

TABLE 1

| Compound of Example No. | Preemergence | | Postemergence | |
|---|---|---|---|---|
| | Pigweed | Foxtail | Pigweed | Foxtail |
| 1 | 2 | 3 | 1 | 1 |
| 2 | | | | |
| 3 | 2 | 1 | 3 | 2 |
| 4 | 4 | 3 | 1 | 1 |
| 5 | 3 | 2 | 2 | 1 |
| 6 | | | | |
| 7 | 3 | 2 | 1 | 1 |
| 8 | 4 | 2 | 1 | 1 |
| 9 | 2 | 2 | 3 | 1 |

The results above show the ability of the compounds of this invention to injure and reduce the vigor of pigweed and foxtail, both of which are widespread weeds which cause losses of many crops in many countries and climates. It will be understood that reducing the vigor of pigweed and foxtail by injuring the individual plants, or by killing part and injuring part of them, is beneficial even though some part of the weed population survives application of the compound. The weeds, the vigor of which has been reduced, are unusually susceptible to the stresses which normally afflict plants, such as disease, drought, lack of nutrients and so forth.

Thus, the treated weeds, even though they survive application of the compound, are likely to expire due to stress of the environment. Further, if the weeds are growing in cropland, the normally growing crop tends to shade out the treated weeds, and therefore has an advantage over the treated weeds in the competition for nutrients and sunlight. Still further, when the weeds are growing in fallow land, or on industrial property which is desired to be bare, the reduction of their vigor necessarily tends to minimize the treated weeds' consumption of water and nutrients, and also minimizes the fire hazard and nuisance presented by the weeds.

The best application rate of a given compound for the control of a given weed varies, of course, depending upon the climate, soil type, water and organic matter contents of the soil and other factors known to plant scientists. It will be found, however, that the optimum application rate is usually in the range of from about 5.0 to about 25.0 kg./ha.

The compounds are applied to the soil or to emerged weeds in the manners usual in agriculture. They may be applied to the soil in the form of either water-dispersed or granular formulations, the preparation of which will be discussed below. Usually, water-dispersed formulations will be used for the application of the compounds to emerged weeds. The formulations are applied with any of the many types of sprayers and granular applicators which are in wide use for the distribution of agricultural chemicals over soil or standing vegetation.

The compounds are normally used in the practice of this invention in the form of herbicidal compositions which are an important embodiment of the invention. An herbicidal composition of this invention comprises a compound of the invention and an inert carrier. In general, the compositions are formulated in the manners usual in agricultural chemistry, and are novel only because of the vital presence of the herbicidal compound.

Very often, the compounds are formulated as concentrated compositions which are applied either to the soil or the foliage in the form of water dispersions or emulsions containing in the range of from about 0.1 percent to about 5 percent of the compound. Water-dispersible or emulsifiable compositions are either solids usually known as wettable powders, or liquids usually known as emulsifiable concentrates. Wettable powders comprise an intimate, finely-divided mixture of the compound, an inert carrier and surfactants. The concentration of the compound is usually from about 10 percent to about 90 percent. The inert carrier is usually chosen from among the attapulgite clays, the montmorillonite clays, the diatomaceous earths and the purified silicates. Effective surfactants, comprising from about 0.5 percent to about 10 percent of the wettable powder, are found among the sulfonated lignins, the condensed naphthalenesulfonates, the naphthalenesulfonates, the alkylbenzenesulfonates, the alkyl sulfates and nonionic surfactants such as ethylene oxide adducts of phenol.

Typical emulsifiable concentrates of the new compounds comprise a convenient concentration of the compound, such as from about 100 to about 500 g. per liter of liquid, dissolved in an inert carrier which is a mixture of water-immiscible solvent and emulsifiers. Useful organic solvents include the aromatics, especially the xylenes, and the petroleum fractions, especially the high-boiling naphthalenic and olefinic portions of petroleum. Many other organic solvents may also be used such as the terpenic solvents, and the complex alcohols such as 2-ethoxyethanol. Suitable emulsifiers for emulsifiable concentrates are chosen from the same types of surfactants used for wettable powders.

When a compound is to be applied to the soil, as for a preemergence application of the compound, it is convenient to use a granular formulation. Such a formulation typically comprises the compound dispersed on a granular inert carrier such as coarsely ground clay. The particle size of granules usually ranges from about 0.1 to about 3 mm. The usual formulation process for granules comprises dissolving the compound in an inexpensive solvent and applying the solution to the carrier in an appropriate solids mixer. Somewhat less economically, the compound may be dispersed in a dough composed of damp clay or other inert carrier, which is then dried and coarsely ground to produce the desired granular product.

We claim:
1. A compound of the formula

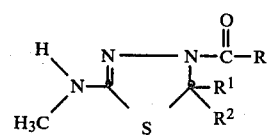

wherein R is phenyl, 3-trifluoromethylphenyl, 2-trifluoromethylphenyl, fluorophenyl, chlorophenyl, nitrophenyl, or $C_3$-$C_4$ alkyl; $R^1$ and $R^2$ are independently hydrogen, methyl or ethyl, provided that one of $R^1$ and $R^2$ is not methyl when the other is ethyl, and provided that no more than one of $R^1$ and $R^2$ is hydrogen.

2. A compound of claim 1 wherein R is t-butyl.

3. The compound of claim 2 wherein $R^1$ and $R^2$ are methyl.

4. A compound of claim 1 wherein $R^1$ and $R^2$ are both methyl.

5. A compound of claim 4 wherein R is phenyl or substituted phenyl.

6. The compound of claim 5 wherein R is phenyl.

7. The compound of claim 5 wherein R is 4-fluorophenyl.

8. The compound of claim 5 wherein R is 2-trifluoromethylphenyl.

9. The compound of claim 5 wherein R is 3-trifluoromethylphenyl.

10. The compound of claim 5 wherein R is 2-fluorophenyl.

* * * * *